United States Patent
Harrie et al.

(10) Patent No.: US 7,044,074 B2
(45) Date of Patent: *May 16, 2006

(54) METHOD AND ARRANGEMENT FOR INSPECTION OF AN OBJECT

(75) Inventors: Per Harrie, Hovas (SE); Johan Fagerholm, Billdal (SE); Michael Kurdve, Vejbystrand (SE); Johan Lindsjo, Abbekas (SE)

(73) Assignee: Tapiren Survey System AB, Billdal (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/811,225

(22) Filed: Mar. 25, 2004

(65) Prior Publication Data

US 2006/0060123 A1   Mar. 23, 2006

Related U.S. Application Data

(63) Continuation-in-part of application No. 10/303,380, filed on Nov. 22, 2002, now Pat. No. 6,712,017, which is a continuation of application No. PCT/SE01/01182, filed on May 25, 2001.

(60) Provisional application No. 60/207,133, filed on May 24, 2000.

(30) Foreign Application Priority Data

May 24, 2000   (SE) .................................... 0001970

(51) Int. Cl.
B63B 59/00   (2006.01)

(52) U.S. Cl. ..................................................... 114/222

(58) Field of Classification Search ................ 114/222, 114/221 R, 312

See application file for complete search history.

(56) References Cited

U.S. PATENT DOCUMENTS

| 3,776,574 | A |   | 12/1973 | Henderson et al. |
| 4,430,568 | A | * | 2/1984  | Yoshida et al. .......... 250/358.1 |
| 4,981,353 | A |   | 1/1991  | Murakawa et al. |
| 5,048,445 | A | * | 9/1991  | Lever et al. ................. 114/222 |
| 6,003,377 | A | * | 12/1999 | Waag et al. .................. 73/625 |
| 6,020,918 | A | * | 2/2000  | Murphy ....................... 348/84 |
| 6,165,283 | A | * | 12/2000 | Dahlin et al. ................. 134/21 |
| 6,196,075 | B1 | * | 3/2001 | Comello et al. ........... 73/865.8 |
| 6,317,387 | B1 |   | 11/2001 | D'Amaddio et al. |
| 6,712,017 | B1 | * | 3/2004 | Harrie et al. ........... 114/221 R |

FOREIGN PATENT DOCUMENTS

JP   8136240   5/1996

* cited by examiner

*Primary Examiner*—Stephen Avila
(74) *Attorney, Agent, or Firm*—Klarquist Sparkman, LLP (57) ABSTRACT

The present invention relates to an inspection system for inspection of an object, comprising at least an image recording means carried by an inspector, a display unit, a storage unit and a contact free positioning unit. The storage unit is arranged to store at least an image taken by said imaged recording unit in relation to a position given by said positioning unit and/or a time index. The inspector may be an underwater diver, remote controlled robot, land vehicle, flight craft, person or the like. The object includes a ship, underwater pipeline, oil pipe, manmade or natural land features, submerged landmarks or the like.

20 Claims, 10 Drawing Sheets

110 { Date: 23/09/99
Start time: 7:4 am

▼ - Attention point
● - Divers position

METHOD AND ARRANGEMENT FOR INSPECTION OF AN OBJECT

CROSS REFERENCE TO RELATED APPLICATION

This is a continuation-in-part of U.S. patent application Ser. No. 10/303,380, filed Nov. 22, 2002 (now U.S. Pat. No. 6,712,017), which is a continuation of International Application No. PCT/SE01/01182, filed May 25, 2001, which claims priority from both Swedish Application No. 0001970-3, filed May 24, 2000, and U.S. Provisional Application No. 60/207,133, filed May 24, 2000.

TECHNICAL FIELD OF THE INVENTION

The present invention relates to an inspection system for inspection of an object, at least comprising an image-recording unit supported by an inspector, a display unit and a storage unit. The invention particularly relates to inspection of ships or the like.

THE STATE OF THE ART

Ships are inspected at close intervals according to law. The inspection typically is carried out in a dock or by divers filming the complete entire bottom of the ship.

At conventional diving inspections, the inspection is usually carried out in the sea, since the visibility is much better there than at the harbours. The person to perform the inspection goes out to the ship in a separate boat, on which all the equipment is brought. At a diving inspection, except for three persons from the diving company, representatives of the classification society and the shipping company are present as well.

During the inspection, the diving company also has divers in the water equipped with a camera and sound transmission equipment and a person supervising the diver. The third person of the diving company monitors a TV screen, together with the representatives of the classification society and the shipping company. The images from the camera of the divers are shown on the TV-screen and stored on a videotape as well. The persons in front of the TV-screen decide which action is to be performed on the ship. At this time, notes are taken on the detected damages and the counting mechanism of the video is recorded.

The diver swims from starboard to the port side, and then moves approximately 2 meters towards the prow, then swims from port to starboard. This pattern is repeated.

The diver keeps track of his position relative to the ship by reading a measuring tape, which is placed in the middle under the ship before the diver started the inspection. The person watching the diver at the TV-screen receives the position of the diver from the diver.

A ship inspection consists of diving work and writing reports for the diving company. The diving work itself takes approximately 8–12 hours for a ship of average-size. After the diving work is completed a report is prepared. It takes about 8 hours to process the videotapes and select frames of the film based on the remarks and writing text corresponding to each remark.

In U.S. Pat. No. 3,776,574, an inspection system for hulls of vessel is described, wherein a diver swims backwards and forwards under the ship and films the hull of the vessel. For orientation and positioning, the hull of the vessel is marked by painting squares and by numbering. At the inspection the areas and their identity numbers are filmed and recorded. As described, this system is time consuming by the marking procedure, the storing and the recovering of information. Criticised areas must be searched and/or registered for manual scanning later on.

SHORT DESCRIPTION OF THE INVENTION

The object of the present invention is to provide a system simplifying the inspection work, reducing the inspection and the reporting time and facilitating the documentation and the search in the documentation.

In the system, according to one preferred embodiment of the invention, the position of a diver is related to the film and this is displayed on a computer monitor, for example.

Additional advantages of the system are:

ensured inspection results, improved control of the position of the inspector or data gathering entity, easier to find specific check points, e.g., valves, etc., the documentation of the diver positions, easy to study specific parts of the inspected object afterwards by clicking on a drawing, less documentation work, generating different reports directly from a computer, appropriate for several applications, e.g., harbour inspections and inspections offshore, and inspections of larger objects on shore, and the system is built in such a way that it is possible to substitute a diver by an ROV (unmanned submarine robot) or any other image recorder carrying entity.

These objects have been solved by the present system which includes a contact free positioning unit and storage unit arranged to store at least an image taken of said image recording unit in relation to a position given by said positioning unit and/or a time index. The system can comprise means for connecting a time and/or position index to said position and image and a note. Moreover, the system can comprise means for digitally storing images and performing a search for an event by means of a time- and/or position- and/or event index.

In one embodiment, the positioning unit comprises: a transmitter/receiver located on a known position adjacent the object to be inspected, a receiver/transmitter located on the inspector, whereby the transmitter/receiver sends out a coded sound signal and the receiver/transmitter responds with a coded signal, which is received by the transmitter/receiver and the position of the receiver/transmitter is decided with assistance of time and direction. Other positioning systems are known from, e.g., U.S. Pat. No. 4,981,353 and JP 81-36240.

In another embodiment, the positioning unit comprises: a number of probes located at known positions, a transmitter located on the inspector, whereby the transmitter sends out a sound signal and the probes receive the signals and decide the position of the transmitter with assistance of a time difference between the probes and known positions are received either by placing the probes on the object or connecting the probes to a positioning system and connecting the object to the positioning system.

In yet another embodiment, the positioning unit comprises: a digital compass module containing a number of magnetic axes and tilting sensors as well, compensating for the inclination of the magnetic axes and that the compass module keeping track of its position.

In an alternative embodiment, the positioning unit comprises: an inertia gyro sensing the direction and speed and keeping track of the position by counting from a given start position.

Preferably, said inspector is a diver or a robot.

The system also includes a database arranged to store the incoming data, comprising a model of the ship, the image taken by the image recording unit, a position of the positioning system, sound of a sound recording unit and remarks provided with time index as well. The input signals of the database comprise amongst others: one or several drawings of the object, which are re-processed to a model of the ship, a sound signal of one or several channels being converted to a standard format and provided with time index, video signal being converted to a standard format and provided with a time index and eventually compressed, position being converted to a relative position and provided with a time index, and remarks, which via a user interface is introduced, is provided with time index and stored.

The invention also refers to a method of inspection of an object by means of a system comprising at least an image recording means carried by an inspector, a display unit and a storing unit. The method comprises providing a contact free positioning unit and a device of the storing unit for at least storing an image recorded of said image recording unit in relation to a position given of said positioning unit and/or a time index.

Moreover, the method comprises the step of connecting a time- and/or position index with said position and image and a note.

Particularly, the invention relates to a method of inspecting a floating object in a medium, particularly a ship, by means of a system comprising at least an image recording unit carried by an inspector, and a computer unit communicating with a storage unit. The method comprises providing a contact free positioning unit at least at the object, and an arrangement of the storage unit for at least storing an image taken of said image recording unit in relation to a position given of said positioning unit and/or a time index. The inspection starts with a digital drawing of the object stored in the computer or a storage unit. The image recording unit and a signal of the positioning unit is connected to the computer. The position of the inspector is shown as a dot on the computer stored drawing. According to a preferred embodiment, the position of the inspector together with an image of the image recording unit is shown substantially continuously while the inspector moves from one position to a second position. In one embodiment, continuous registration of the position of the inspector is carried out. Preferably, at the appearance of a remark being stored and connected with an image, captions and at least a part of the drawing are connected with the position of the drawing. At the study of the inspection data including notes is recovered by pointing at a drawing corresponding said drawing by means of an indicator in a registered movement pattern of the inspector.

SHORT DESCRIPTION OF THE DRAWINGS

In the following, the invention will be described with reference to the embodiments shown in the enclosed drawings, in which.

DESCRIPTION OF THE EMBODIMENTS

In the following, the invention is described with reference to a first embodiment relating to a system being used to inspect ships. However, the invention can be used to inspect and examine different objects.

Figure 1:
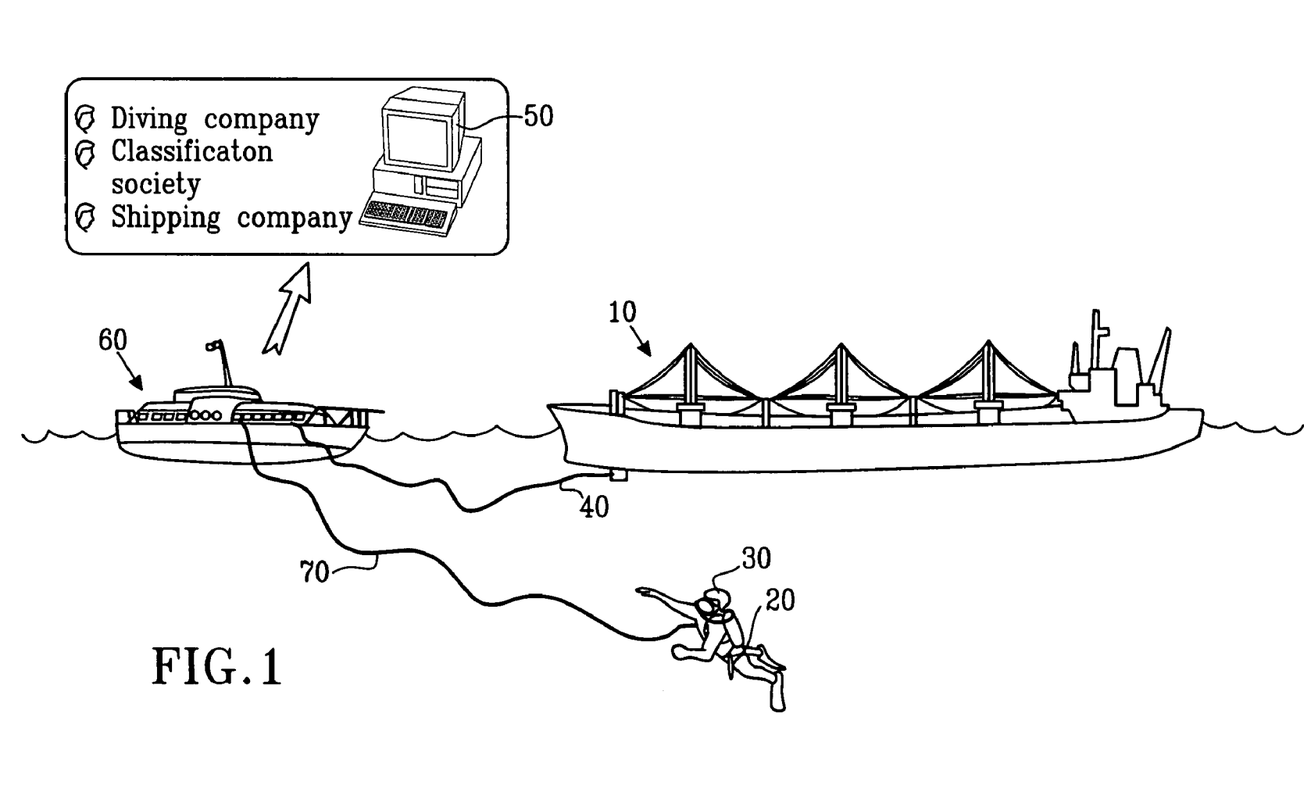
FIG. 1 schematically shows a first embodiment of a system according to the present invention.

A system for inspection of, e.g., a ship 10 (or another floating object or immersed in a volume) according to the invention is shown in FIG. 1 preferably comprises a sound and image recording unit 30 of a diver 20, a positioning unit 40 and a computer unit 50.

The diver 20 carries conventional diving equipment provided with a communication means and a camera 30 located, for example, on the helmet for recording images and sound, for facilitating the inspection work.

The camera 30 can be a conventional submarine camera supplying analog and/or digital images and sound as well. However, the sound recording can be carried out by means of separate equipment. The communication between the (liver and the inspection ship 60 can be performed via cables 70 and/or wireless means via radio.

The positioning unit can consist of any positioning system. Preferably, one or more of the following systems can be used. However, other equipment appropriate for the invention can also be present.

The positioning system can comprise:

Ultra short baseline (USBL): a transmitter/receiver is placed on a known position. A transfer is placed on the diver or the ROV. The transmitter/receiver sends a coded sound signal. The transponder responds with a coded signal. The transmitter/receiver receives the signal and decides the position of the transponder with assistance of the time and direction.

Long Base Line (LBL): a number of probes are placed on known positions. A transmitter is located on the diver or the ROV. The transmitter sends a sound signal; the four probes receive the signal and decide the position of the transmitter with assistance from the time difference between the probes. The known positions are received either by placing the probes against, e.g., the ship or connecting these with the GPS system and connecting the ship with the GPS system.

Digital Compass module: the system comprises a digital compass module containing three magnetic axes and two tilting sensors. The tilting sensors compensate for the inclination of the magnetic axes. The compass module keeps track of its position. A digital compass module can be used, e.g., on a ROV if it is completed with a speedometer. By the fact that the direction and the speed of the ship is known, the position can be calculated. The module must be provided with a start position. However, a magnetic compass module is not considered as appropriate when, e.g., a ship can interfere the magnetic field.

Inertia gyro can be used in several military applications. The gyros sense the acceleration from which you can derive the direction and the speed, and keeps track of the position by calculating from a given start position.

Figure 2:
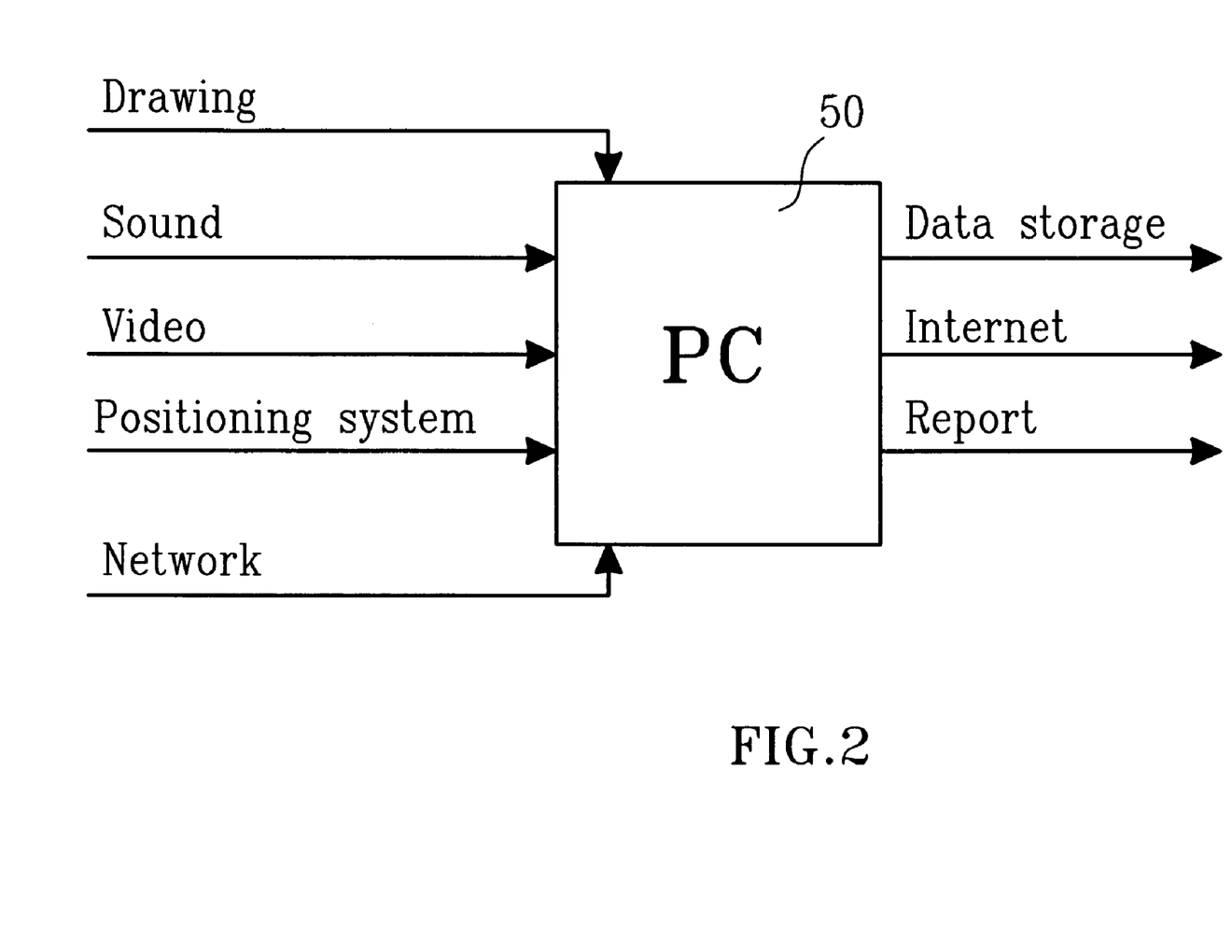
FIG. 2 shows a comprehensive block diagram of the system according to the invention.

FIG. 2 shows a block diagram of the computer unit 50. A video (camera), sound recording unit, positioning system signal, drawing basis from a drawing data base and eventually another communications means, such as a network communication, are directly or indirectly connected to the computer unit. Data processed in the data unit is transferred as a report to a storage unit, via for example a network connected to an intranet or the Internet. The system also gives an opportunity for performing the inspection at a distance, i.e., representatives of the diving company, the classification society or the shipping company do not need to be present on the accompanying boat, but can follow the inspection via the Web.

Figure 3:
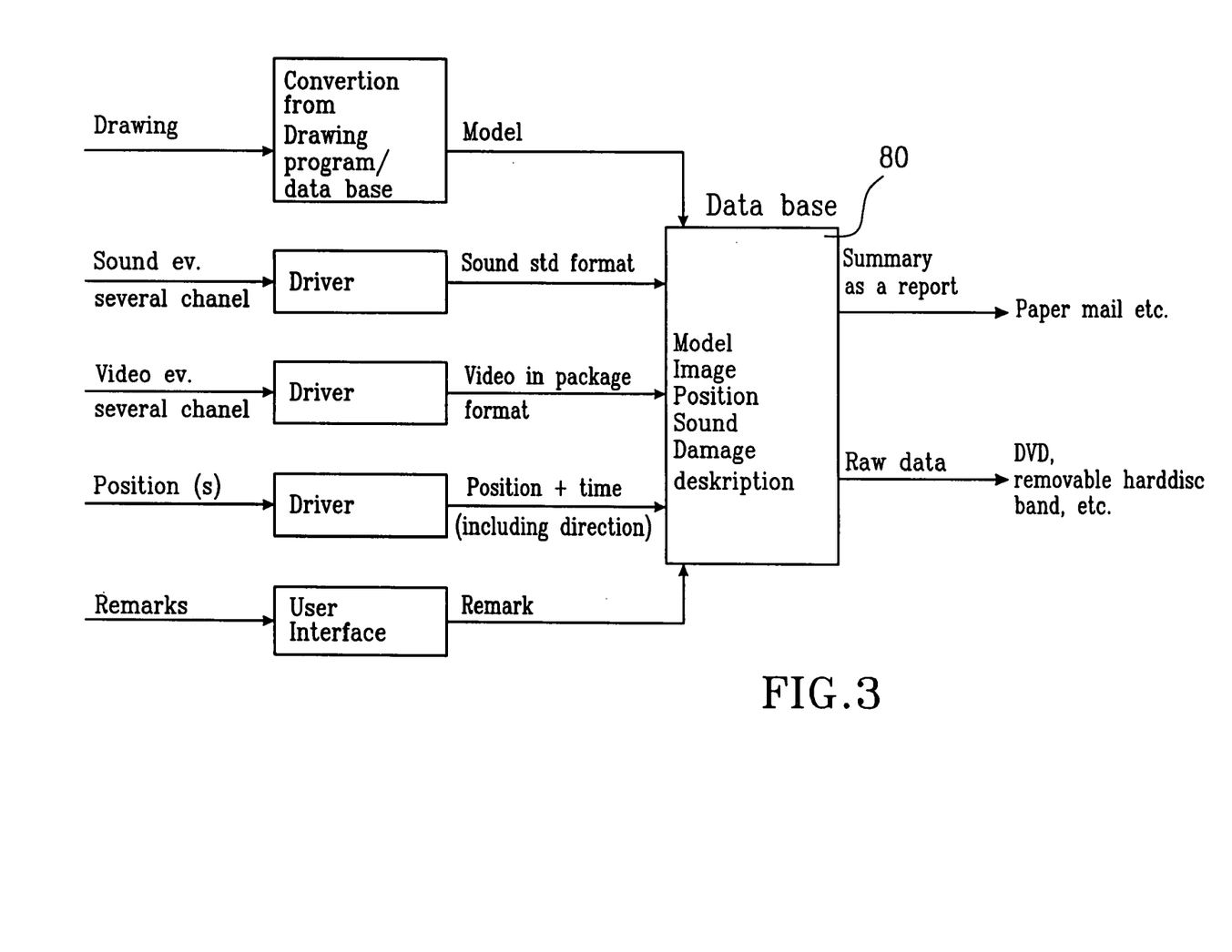
FIG. 3 shows a comprehensive block diagram of the storage part in the computer system according to the invention.

The database 80, being schematically shown in FIG. 3, is arranged to store the incoming data, preferably processed data. In the database a model of the ship is stored, the film recorded by the camera of the diver, the position of the positioning system, the sound of the sound recording unit and remarks are provided with time index before they are stored. Consequently, the input signals of the database comprise:

one or several drawings of the ship, which are re-processed to a model of the ship,
sound from one or several channels, which are converted to a standard format and provided with time- and/or position index by means of, e.g., a driving routine,
video signal of one or several channels being converted to a standard format and provided with time- and/or position index, and are eventually compressed, by means of, e.g., a driving routine,
position being converted to a relative position and provided with time- and/or position index by means of, e.g., a driving routine, and
remarks, e.g., compensation remarks, being introduced via a user's interface and provided with time/or position index and stored.

A report can be put together from the database and data can be stored in all external medium, preferably in digital form, such as DVD, a detachable hard disc, DAT or the like.

Figures 4A, 4B:
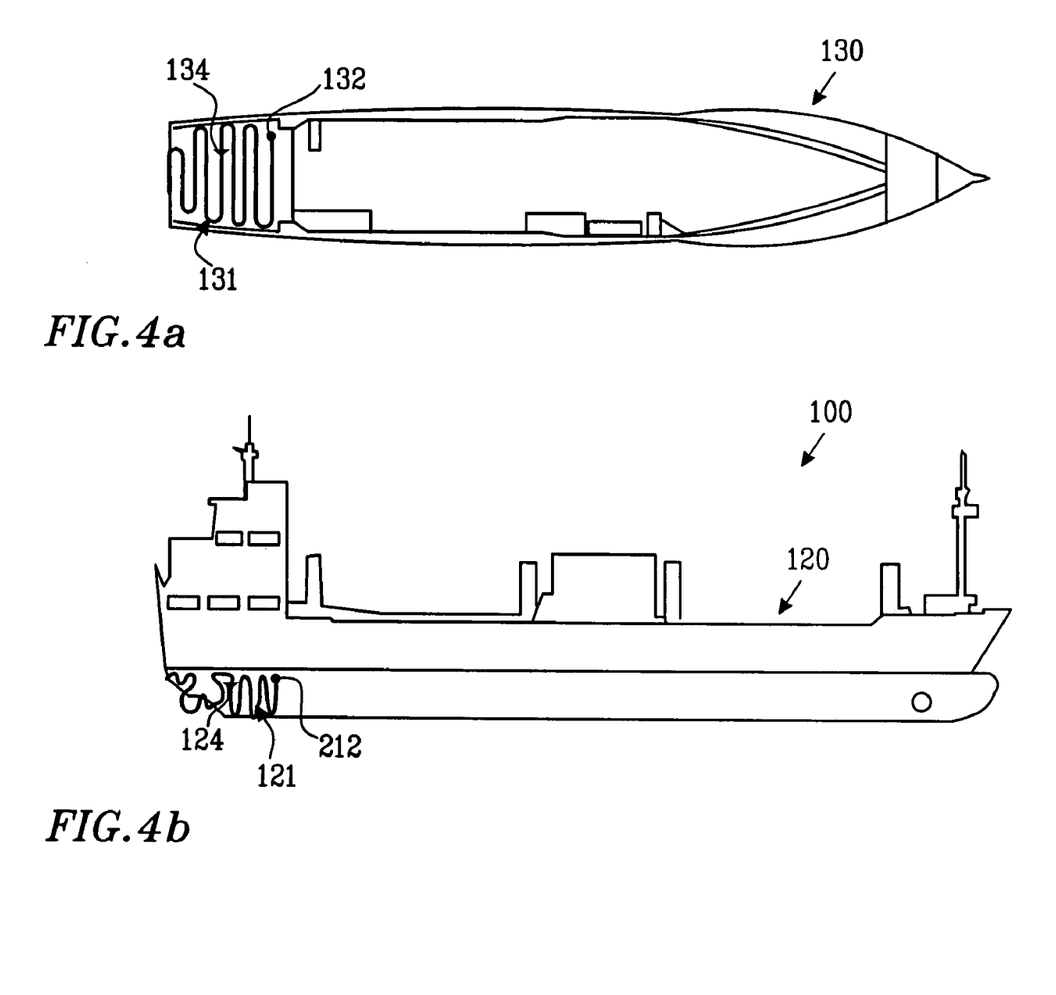
FIG. 4 shows a screen layout in the system according to the invention, FIG. 5 schematically shows a second embodiment of a system according to the present invention.
Figures 4C, 4D, 4E:
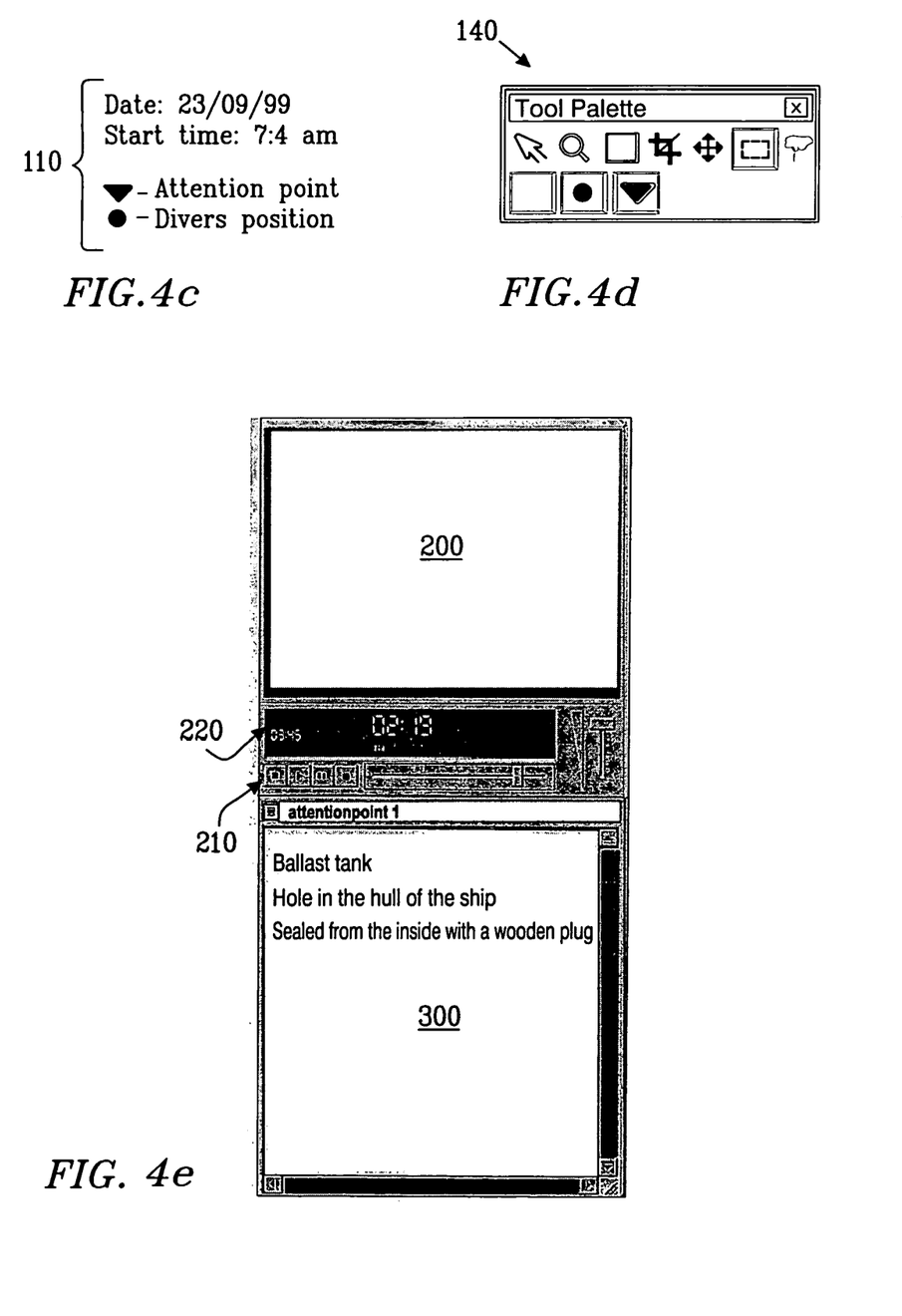

FIG. 4 shows a screen layout of the inspection. The layout comprises a number of fields:

in a main field 100 a drawing of the ship is shown, both a side-view and a view from above (other views are also possible),
in a second field 200 the images of the camera are shown, and
in a third field 300 the remarks are shown in form of text.

By the fact that a digital storing is used the damages can be associated with the images and a quick search and processing are provided.

In the main field 100, further information is present. In a lower field 110, a key to the signs is shown concerning the ship being inspected and time/date for the start of the inspection as well.

The model of the ship 120 and 130, shown in the main field, is provided with a trace 121/131 showing the distance run or path of the diver, the position of the diver 212/132 and the position for possible remarks. By using two views, a "three-dimensional" position is obtained with respect to the ship. The main field may also comprise a toolbar 140 for zooming in or out, displacement of views, copying, etc.

Except for the viewing screen, the image and video field 200 also comprise means 210 for controlling the image, such as playback, storing, winding and the like. The time is also stated in a field 220.

The remark field 300 is really a notepad wherein it is possible to introduce information, e.g., via the keyboard, which is connected together with the shown image and the position of the diver via time index.

The function of the system is described in the following non-limited example: The inspection work starts with a digital drawing of the ship 10 being stored in the computer 50 (new ships have digital drawings, the drawings are scanned for older ships). The computer replaces the TV-screen in a conventional inspection.

The video camera 30 and a signal of the positioning system 40 are connected to the computer. The position of the driver is shown as a dot on the drawing being data stored.

The people following the inspection from the accompanying ship 60 (FIG. 1) see the position of the diver together with the video film (field 200, FIG. 4) all the time, while the diver swims from one side to another side. Observers have the ability to verify any place where the diver films, making it easier to help the diver find particular locations on the ship and verify that the diver has been everywhere.

A still picture is stored and connected together with all remarks, captions and a drawing having the position of the damage. This information is immediately printed after the inspection has concluded. The total work is stored on a storing media, such as a DVD disc. Consequently, report writing is simplified for each inspection.

When studying inspection data, one only needs to click, by means of a mouse or the like, on the part of line 124/134 representing the position for which data is desired. This is preferable to prior systems which require reviewing the video until the correct position on the ship is found. The video for a single inspection is about eight hours.

Figure 5:
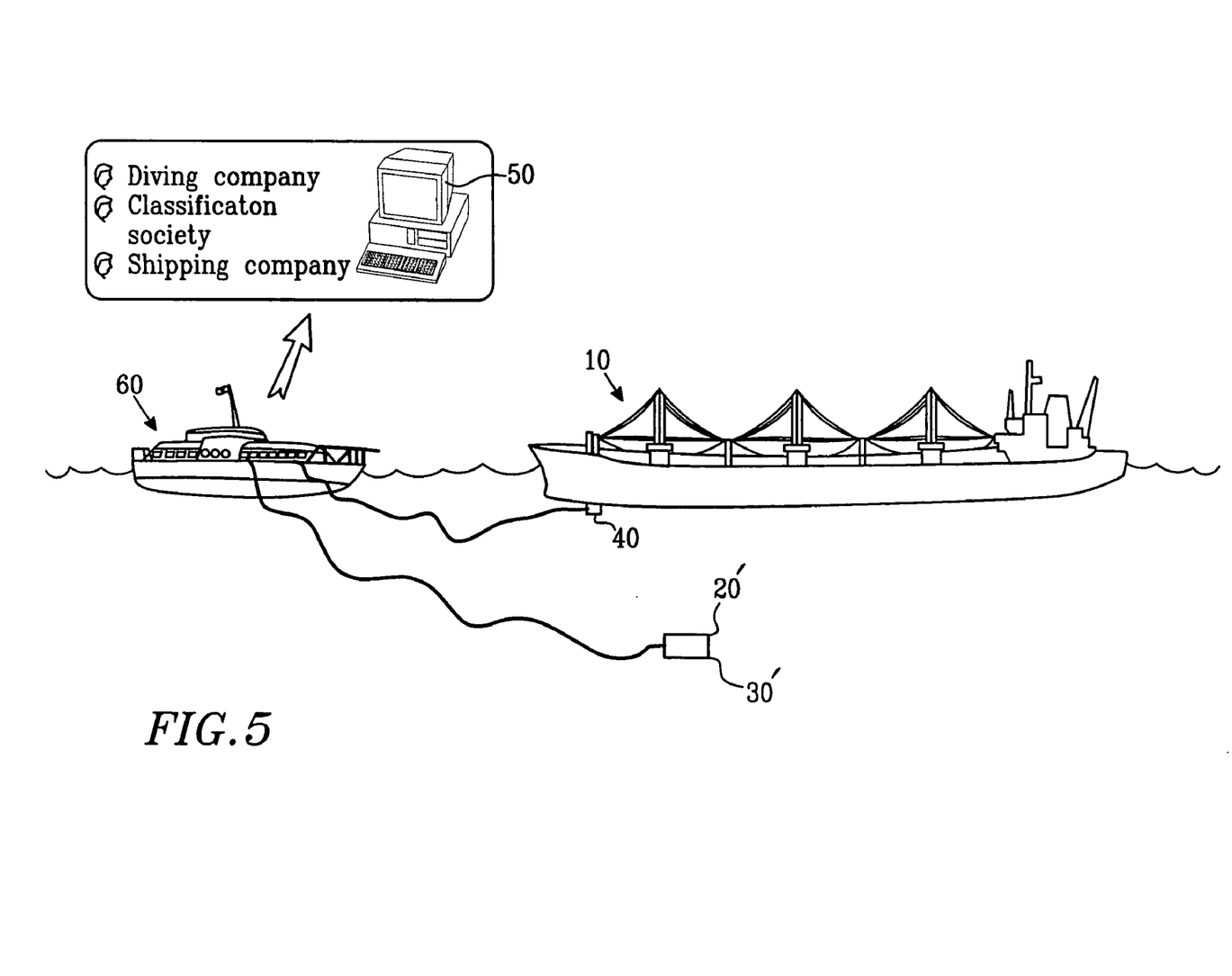

Of course, the diver can be replaced with a robot 20' and so-called ROV containing an image-/sound recording unit 30' such as illustrated in FIG. 5. In this case, a means is arranged for controlling the robot from the inspection ship.

Figure 6:
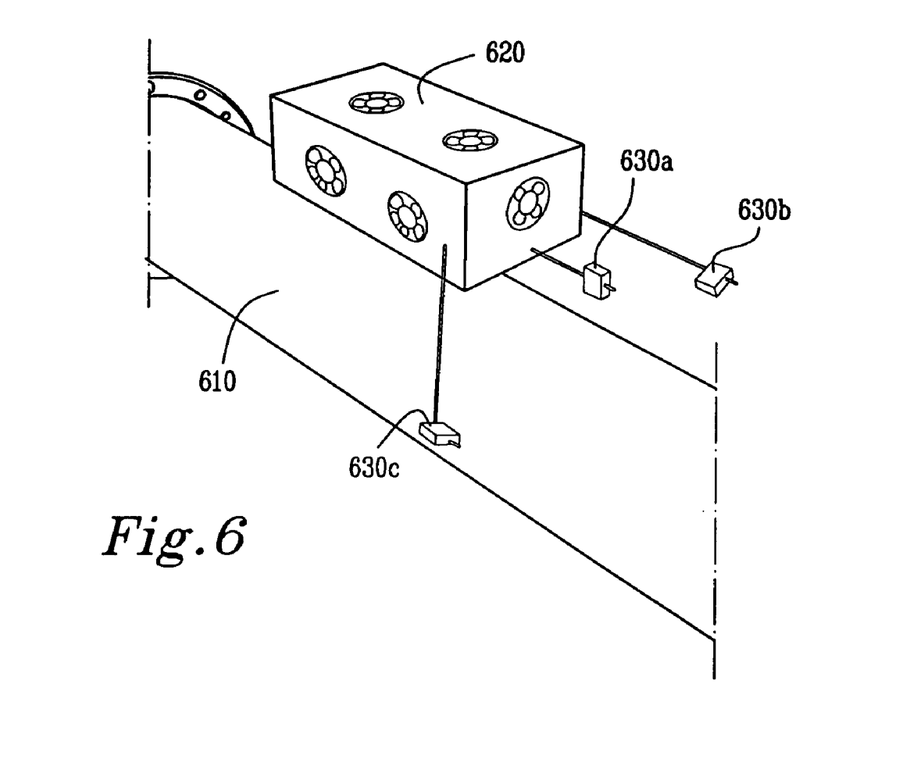
FIGS. 6–13 illustrate other applications and features of the invention.

As mentioned above, the ROV can be used in other fields. One application is illustrated in FIG. 6. In this case, an ROV 620 is provided with three cameras 630a–630c on a holders extending from the ROV. The ROV is used for inspecting a submerged pipe, such as an oil pipe in the seabed. The cameras are arranged in such way that they can record images from top, left and right sides of the pipe. The ROV is controlled from an inspection boat (not shown) and transmits images to the inspection boat for recording.

Figure 7:
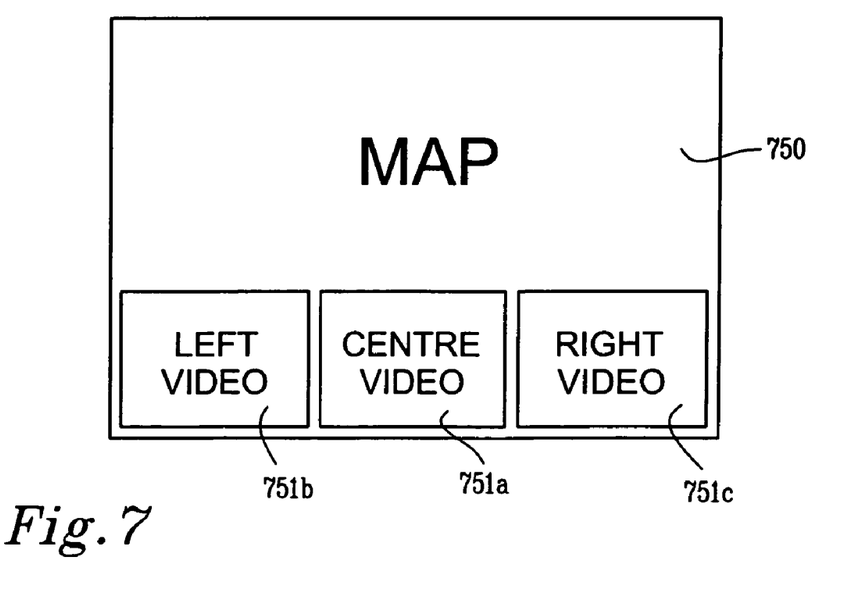

FIG. 7 is an example of an inspection display picture at the inspection boat. The picture comprises a map 750 and images 751a–751c from the three cameras. In the same way as the earlier embodiment, the defects or other events of interest are recorded with a notation associated to the position/time/event.

The invention may also be used for inspection of pipes from inside, e.g., by means of a robot traveling inside the pipe, and storing or sending informational to an inspection unit.

Figure 8:
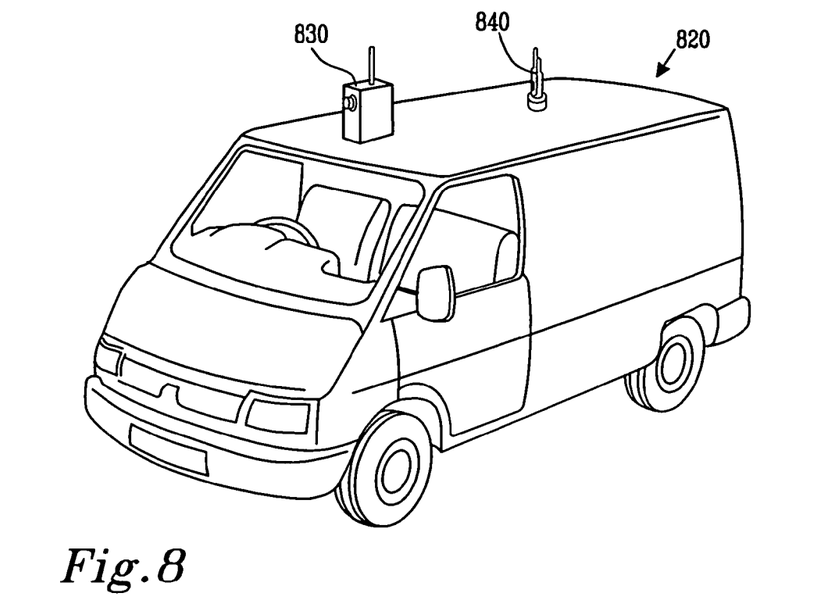

Yet another application is illustrated in FIG. 8. In this case a vehicle 820 is provided with a camera 830 on the roof of the vehicle. The vehicle is used for inspecting roads or the surroundings. The position of the vehicle is provided with a positioning system such as GPS (GPS antenna 840). An inspector, e.g., in the vehicle receives images from the camera.

Figure 9:
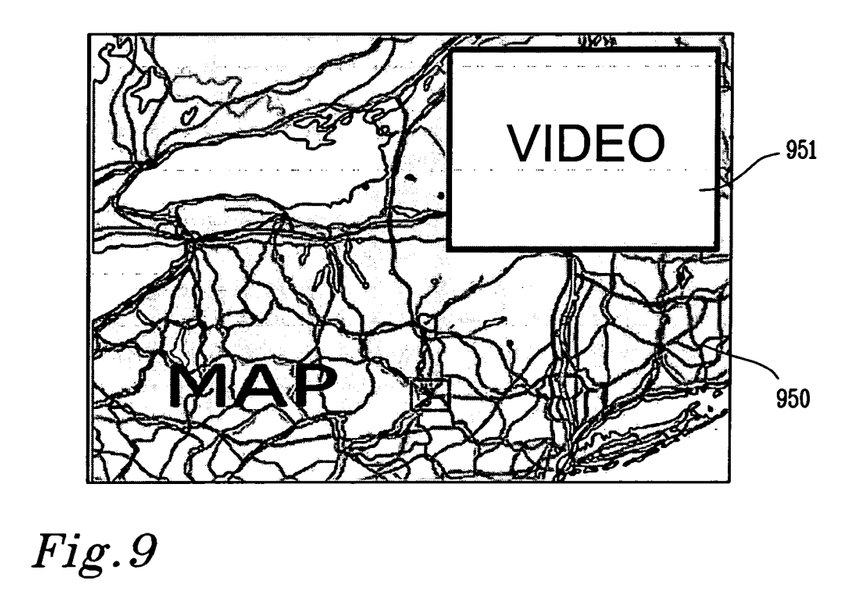

FIG. 9 is an example of an inspection display picture in the vehicle. The picture comprises a map 950 and a video image 951 from the camera. The map is connected to the positioning system recording the position of the vehicle. In the same way as the earlier embodiment, events of interest are recorded with a notation associated to the position/time/event.

Figure 10:
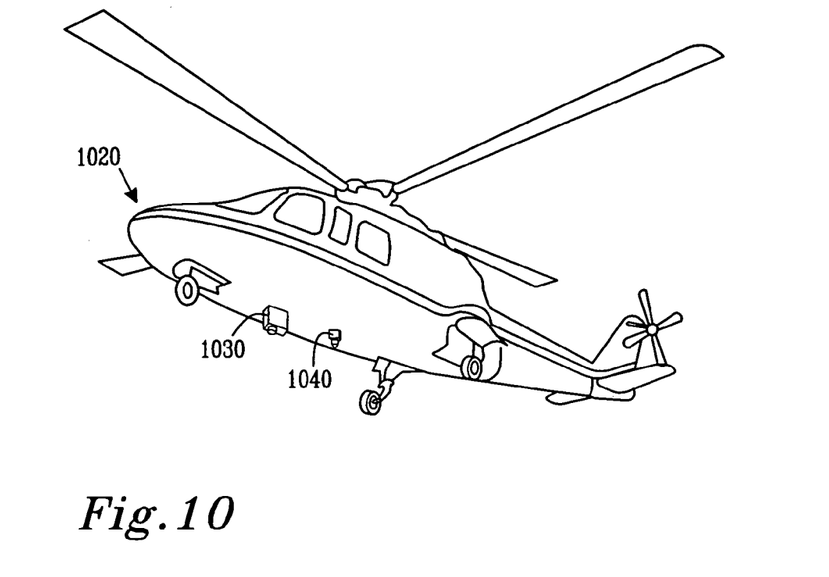

Yet another application is illustrated in FIG. 10. In this case a helicopter 1020 (or airplane) is provided with a camera 1030 under the cockpit. The helicopter is used for inspecting roads, power lines, bridges, forest etc. The position of the helicopter is provided with a positioning system such as GPS (GPS antenna 1040). An inspector, e.g., in the helicopter receives images from the camera. The helicopter is given as an example and any other flying craft can be used.

Figure 11:
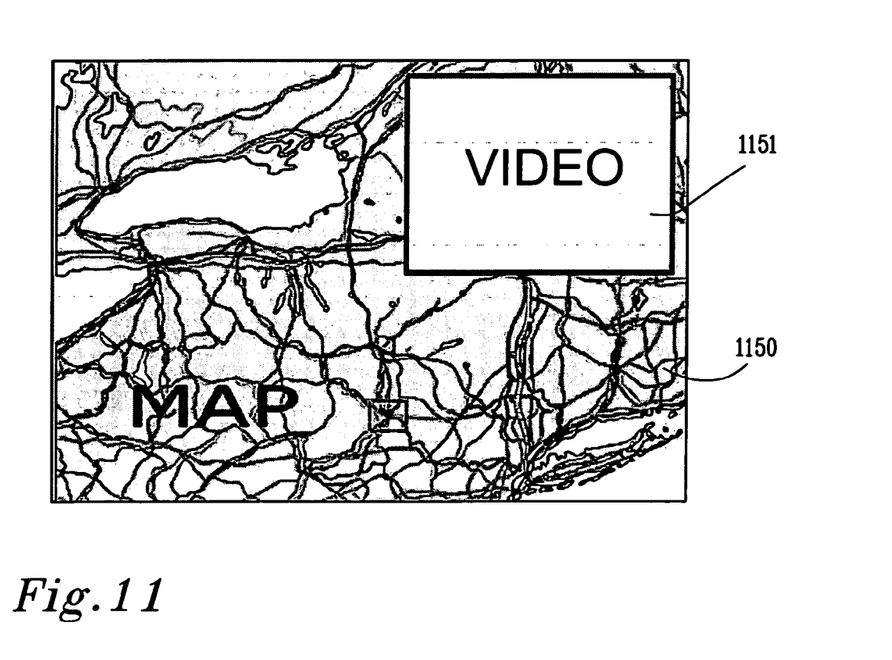

FIG. 11 is an example of an inspection display picture in the helicopter or a remote location. The picture comprises a map 1150 and a video image 1151 from the camera. The map is connected to the positioning system recording the position of the helicopter. In the same way as the earlier embodiment, events of interest are recorded with a notation associated to the position/time/event.

Figure 12:
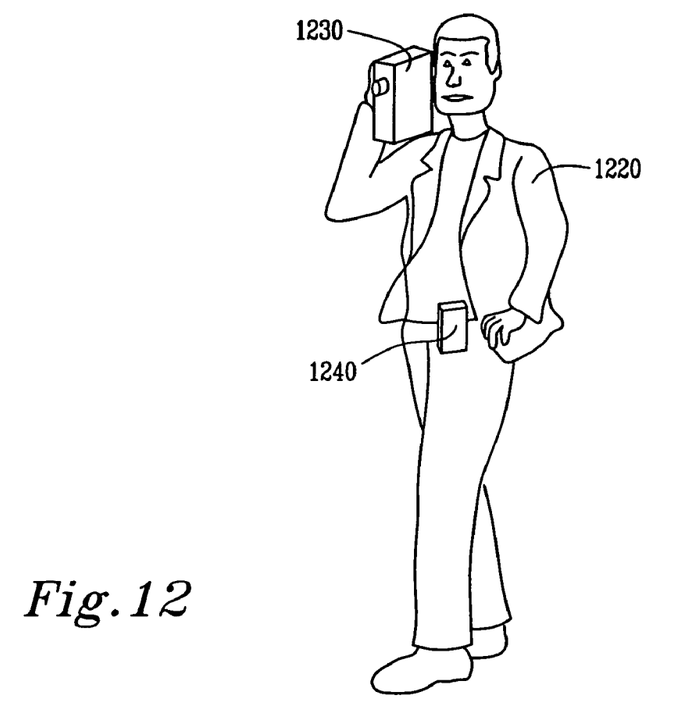

In the embodiment of FIG. 12, a person 1220 uses a camera 1230 for inspection and/or recording. The person can record or inspect roads, streets, etc. The position of the person is provided with a positioning system such as GPS (GPS positioning device 1240). The camera may be connected to or comprise a computer unit. The person leaves notes, e.g., orally.

Figure 13:
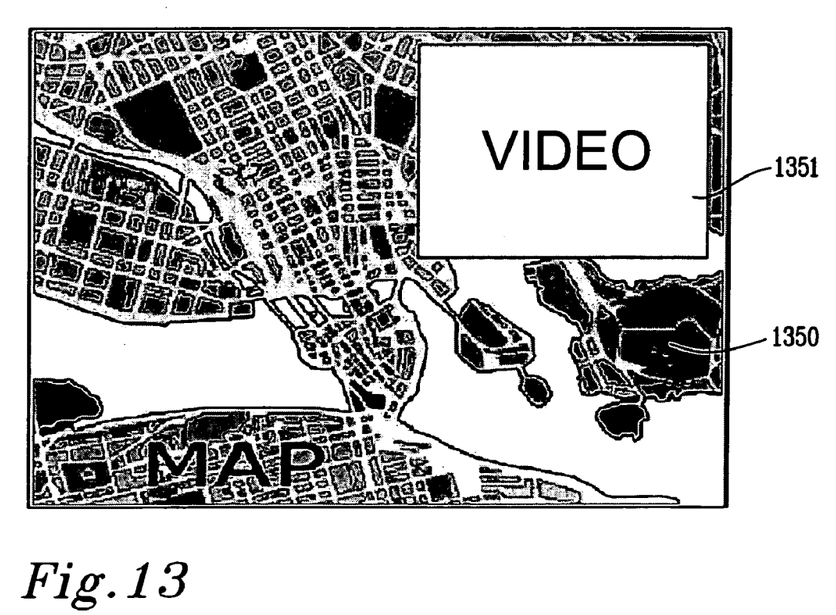

FIG. 13 is an example of an inspection display picture in the computer. The picture comprises a map 1350 and a video image 1351 from the camera. The map is connected to the positioning system recording the position of the person, e.g., on a street map. In the same way as the earlier embodiment, events of interest are recorded with a notation associated to the position/time/event. Tourists visiting a city, etc., may also use this application. In this case, a tourist can use the system to record a tour and also add comments, e.g., orally, to the recorded tour.

While we have illustrated and described preferred embodiments of the invention, it is realized that several variations and modifications are possible within the scope of the accompanying patent claims.

The invention claimed is:

1. An inspection system for inspection of an object, comprising:
   at least one image recording unit carried by an inspector,
   a display unit,
   a storage unit and
   a contact free positioning unit,
   the storage unit being arranged to store at least one image taken by said image recording unit in relation to a position given by said positioning unit and/or a time index, said system further including means for storing images digitally and performing a search for an event by means of a time, position and/or event index, and means for connecting a time and/or a position index with said position and image and a note, wherein said image recording unit is arranged to be movable on an inspecting entity.

2. The system as claimed in claim 1, further comprising means for storing images digitally and performing a search for an event by means of a time, position and/or event index.

3. The system as claimed in claim 1, wherein said positioning unit comprises:
   a transmitter/receiver placed at a known position adjacent the object to be inspected,
   a receiver/transmitter placed on said inspecting entity, whereby the transmitter/receiver sends a coded sound signal and the receiver/transmitter responds with a coded signal, which is received by the transmitter/receiver and the position of the receiver/transmitter is decided with assistance of time and direction.

4. The system as claimed in claim 1, wherein said positioning unit comprises:
   a number of probes placed at known positions, a transmitter placed on the inspecting entity, whereby the transmitter sends a sound signal, and the probes receive the signal and decide the position of the transmitter with assistance from a time difference between the probes, and the known positions are received either by placing the probes against the object or connecting the probes to a positioning system to which the object is connected.

5. The system as claimed in claim 1, wherein said positioning unit comprises:
   a digital compass module which includes a number of magnetic axes and tilting sensors and compensates for the inclination of the magnetic axes, such that the compass module keeps track of its position.

6. The system as claimed in claim 1, wherein said positioning unit includes an inertia gyro to sense direction and speed, and to keep track of its position with reference to a given start position.

7. The system as claimed in claim 1, wherein said inspecting entity is a diver.

8. The system as claimed in claim 1, wherein said inspecting entity is a robot.

9. The system as claimed in claim 1, further comprising a database arranged to store incoming data including a model of the object, one or more images recorded by the image recording unit, a position of the positioning unit, sound from a sound recording unit and remarks provided with time index.

10. The system as claimed in claim 9, wherein input signals of the database comprise:
    (a) one or more drawings of the object which comprises a ship, which are re-processed to a model of the ship,
    (b) sound on one or more channels, which are converted to a standard format and provided with a time index,
    (c) video signal which is converted to a standard format, provided with time index and eventually compressed,
    (d) position being converted to a relative position provided with a time index, and
    (e) remarks which are brought in via a user interface, provided with a time index and stored.

11. The system as claimed in claim 1, wherein said positioning means is a GPS (Global Positioning System base).

12. A submarine based inspection system for inspection of an object, comprising:
    at least one image recording unit carried by a robot,
    a storage unit and
    a positioning unit,
    the storage unit being arranged to store at least one image taken by said image recording unit in relation to a position given by said positioning unit and/or a time index, said system further including means for storing images digitally and performing a search for an event by means of a time, position and/or event index, and means for connecting a time and/or a position index with said position and image and a note, wherein said image recording unit is arranged to be movable on an inspecting entity.

13. The system of claim 12, wherein said robot is arranged with three image recorders.

14. The system of claim 12, wherein said object is a pipeline.

15. An air based inspection system arranged on a flying craft for inspection of an object, comprising:

at least one image recording unit carried by said flying craft, a storage unit and a positioning unit, the storage unit being arranged to store at least one image taken by said image recording unit in relation to a position given by said positioning unit and/or a time index, said system further including means for storing images digitally and performing a search for an event by means of a time, position and/or event index, and means for connecting a time and/or a position index with said position and image and a note, wherein said image recording means is arranged to be movable on an inspecting entity.

16. The system of claim 15, wherein said object includes roads, overhead power lines, forests, bridges, and/or geographic features.

17. A ground based inspection system arranged on a vehicle for inspection of an object, comprising:

at least one image recording unit carried by said vehicle, a storage unit and a positioning unit, the storage unit being arranged to store at least one image taken by said image recording unit in relation to a position given by said positioning unit and/or a time index, said system further including means for storing images digitally and performing a search for an event by means of a time, position and/or event index, and means for connecting a time and/or a position index with said position and image and a note, wherein said image recording means is arranged to be movable on an inspecting entity.

18. The system of claim 17, wherein said object includes roads, overhead power lines, forests, bridges, and/or geographic features.

19. A ground based inspection system carried by a person for inspection or event recording, comprising:

at least one image recording unit carried by said person, a storage unit and a positioning unit, the storage unit being arranged to store at least one image taken by said image recording unit in relation to a position given by said positioning unit and/or a time index, said system further including means for storing images digitally and performing a search for an event by means of a time, position and/or event index, and means for connecting a time and/or a position index with said position and image and a note, wherein said image recording means is arranged to be movable on an inspecting entity.

20. A system for inspection of interior of a pipe system, comprising:

at least one image recording unit carried by a robot, a storage unit and a positioning unit, the storage unit being arranged to store at least one image taken by said image recording unit in relation to a position given by said positioning unit and/or a time index, said system further including means for storing images digitally and performing a search for an event by means of a time, position and/or event index, and means for connecting a time and/or a position index with said position and image and a note, wherein said image recording means is arranged to be movable on an inspecting entity.

* * * * *